(12) United States Patent
Russo (10) Patent No.: US 8,920,312 B2
(45) Date of Patent: Dec. 30, 2014

(54) TRIANGULATION MECHANISM FOR ACCESS PORTS

(75) Inventor: Mark Russo, Plantsville, CT (US)

(73) Assignee: Covidien LP, Mansfield, MA (US)

( * ) Notice: Subject to any disclaimer, the term of this patent is extended or adjusted under 35 U.S.C. 154(b) by 299 days.

(21) Appl. No.: 13/412,107

(22) Filed: Mar. 5, 2012

(65) Prior Publication Data

US 2012/0253383 A1    Oct. 4, 2012

Related U.S. Application Data

(60) Provisional application No. 61/469,028, filed on Mar. 29, 2011.

(51) Int. Cl.
*A61B 17/34* (2006.01)
*A61B 17/29* (2006.01)

(52) U.S. Cl.
CPC ..... *A61B 17/3423* (2013.01); *A61B 2017/2927* (2013.01); *A61B 2017/3405* (2013.01); *A61B 2017/2905* (2013.01); *A61B 2017/2906* (2013.01); *A61B 2017/3452* (2013.01)
USPC .......................................... 600/184; 606/130

(58) Field of Classification Search
CPC ............ A61B 17/00; A61B 1/06; A61B 1/31; A61B 1/32
USPC .......... 600/184; 606/108, 130, 139, 144–150, 606/167, 190, 198
See application file for complete search history.

(56) References Cited

U.S. PATENT DOCUMENTS

| 5,269,772 | A  |    | 12/1993 | Wilk |         |
|-----------|----|----|---------|------|---------|
| 5,318,013 | A  |    | 6/1994  | Wilk |         |
| 8,343,047 | B2 | *  | 1/2013  | Albrecht et al. | 600/206 |
| 8,641,610 | B2 | *  | 2/2014  | Okoniewski et al. | 600/208 |
| 8,684,918 | B2 | *  | 4/2014  | Stopek | 600/215 |
| 2005/0234294 | A1 |  | 10/2005 | Saadat et al. | |
| 2007/0167680 | A1 |  | 7/2007  | Miyamoto et al. | |
| 2008/0188868 | A1 |  | 8/2008  | Weitzner et al. | |
| 2009/0012477 | A1 |  | 1/2009  | Norton et al. | |
| 2010/0228094 | A1 | * | 9/2010 | Ortiz et al. | 600/205 |
| 2010/0240960 | A1 |  | 9/2010  | Richard | |
| 2010/0286484 | A1 | * | 11/2010 | Stellon et al. | 600/208 |
| 2012/0157785 | A1 | * | 6/2012  | Kleyman | 600/208 |

* cited by examiner

*Primary Examiner* — Julian W Woo
*Assistant Examiner* — Lucas Paez (57) ABSTRACT

A surgical apparatus and method for triangulation is disclosed which includes a housing, a rod extending through the housing and a plate attached to a distal end of the rod. The housing is adapted for sealed insertion into an incision in tissue and defines a longitudinal axis. The plate is rotatable about the longitudinal axis upon rotation of the rod and includes a plurality of slots dimensioned for the reception of surgical objects therethrough. Each of the slots is adapted to transition a surgical object between a first position and a second position upon rotation of the plate. The plate is movable relative to the housing along the longitudinal axis upon actuation of the rod in an axial direction and the plate may also be removably attachable to a distal end of the housing.

22 Claims, 6 Drawing Sheets

TRIANGULATION MECHANISM FOR ACCESS PORTS

CROSS REFERENCE TO RELATED APPLICATIONS

The present application claims the benefit of and priority to U.S. Provisional Application Ser. No. 61/469,028, filed on Mar. 29, 2011, the entire contents of which are incorporated herein by reference.

BACKGROUND

1. Technical Field

The present disclosure relates generally to surgical instruments for use with a seal anchor member. More particularly, the present disclosure relates to articulating surgical instruments usable with a seal anchor member that provides multiple instrument access through a single incision in a minimally invasive surgical procedure.

2. Description of Related Art

Increasingly, many surgical procedures are performed through small incisions in the skin. As compared to the larger incisions typically required in traditional procedures, smaller incisions result in less trauma to the patient. By reducing the trauma to the patient, the time required for recovery is also reduced. Generally, the surgical procedures that are performed through small incisions in the skin are referred to as endoscopic. If the procedure is performed on the patient's abdomen, the procedure is referred to as laparoscopic. Throughout the present disclosure, the term minimally invasive is to be understood as encompassing both endoscopic and laparoscopic procedures.

During a typical minimally invasive procedure, surgical objects, such as surgical access devices (e.g., trocar and cannula assemblies) or endoscopes, are inserted into the patient's body through the incision in tissue. In general, prior to the introduction of the surgical object into the patient's body, insufflation gas is used to enlarge the area surrounding the target surgical site to create a larger, more accessible work area. Accordingly, the maintenance of a substantially fluid-tight seal is desirable so as to inhibit the escape of the insufflation gas and the deflation or collapse of the enlarged surgical site. In response to this, various access devices with sealing features are used during the course of minimally invasive procedures to provide an access for surgical objects to enter the patient's body. Each of these devices is configured for use through a single incision or a naturally occurring orifice (i.e. mouth, anus, or vagina) while allowing multiple instruments to be inserted through the device to access the working space beyond the device.

During procedures employing multiple surgical instruments through a single incision access device, it is advantageous to determine the position of the end effectors relative to each other and/or relative to a fixed reference point. This is desirable when one or more of the instruments includes an end effector that is articulable relative to the surgical instrument. Identifying the position of each end effector relative to the other end effectors and/or a common reference point is advantageous during a surgical procedure.

One example, as disclosed by U.S. Publication No. 2005/0234294, uses an articulating element disposed near a distal region and pivotally coupled to hinges by linkages.

Another example, as disclosed by U.S. Publication No. 2007/0167680 and U.S. Publication No. 2008/0051631, uses a rod connected to linking members which spread a set of arm members containing surgical devices apart when the rod is actuated.

Another example, as disclosed by U.S. Publication No. 2008/0188868, uses a collar, a wedge, a balloon or bands to help maintain a divergence between the surgical devices.

Yet another example, as disclosed by U.S. Pat. Nos. 5,318,013; 5,395,367; and 5,511,564, uses an actuator including an articulated linking comprising a pair of arms pivotally connected to a push rod and to shafts of respective grasping forceps to enable relative spreading of the grasping forceps from a straightened or mutually parallel configuration to a spread use configuration.

However, a continuing need exists for determining the relative positions of the end effectors of articulating surgical instruments used with an access device that permits multiple instruments to be used through a single incision.

SUMMARY

A surgical apparatus is disclosed which includes a housing, a rod extending through the housing and a plate attached or coupled to a distal end of the rod. The housing is adapted for sealed insertion into an incision in tissue and defines a longitudinal axis. The housing includes a plurality of lumens extending therethrough which are adapted for the sealed reception of surgical objects.

The plate is rotatable about the longitudinal axis upon rotation of the rod and includes a plurality of slots dimensioned for the reception of surgical objects therethrough. Each of the slots is adapted to transition a surgical object between a first position and a second position upon rotation of the plate. The plate is movable relative to the housing along the longitudinal axis upon actuation of the rod in an axial direction and the plate may also be removably attachable to a distal end of the housing.

At least one of the slots is dimensioned such that the second position is farther from the longitudinal axis than the first position. Alternatively at least one of the slots is dimensioned such that the second position is closer to the longitudinal axis than the first position or that the second position is the same distance from the longitudinal axis as the first position. The slots may define a variety of shapes including but not limited to a kidney shape, an arcuate shape, a linear shape or any other geometric shape. A portion of each slot may be aligned with a respective lumen of the plurality of lumens when in the first position and at least one slot may be shaped differently than at least one other slot.

A method of triangulation using the surgical apparatus is also disclosed, the method including the steps of providing a housing, a rod extending through the housing and plate attached to a distal end of the rod as discussed above, inserting surgical objects through one or more of the lumens and slots, actuating the rod axially and rotating the rod. When actuating the rod axially, the plate is moved relative to the housing along the longitudinal axis. When the rod is rotated, the plate is rotated and the surgical objects are transitioned between the first position and the second position.

At least one of the slots may be dimensioned such that the second position is farther from the longitudinal axis than the first position. Alternatively, at least one of the slots may be dimensioned such that the second position is closer to the longitudinal axis than the first position or that the second position is the same distance from the longitudinal axis as the first position. The slots may define a variety of shapes including but not limited to a kidney shape, an arcuate shape, a linear shape or any other geometric shape.

The various aspects of this disclosure will be more readily understood from the following detailed description when read in conjunction with the appended drawings.

BRIEF DESCRIPTION OF THE DRAWINGS

The accompanying drawings, which are incorporated in and constitute a part of this specification, illustrate embodiments of the invention, and together with a general description of the invention given above, and the detailed description of the embodiments given below, serve to explain the principles of the invention.

DETAILED DESCRIPTION

Particular embodiments of the presently disclosed surgical apparatus are described in detail with reference to the drawing figures wherein like reference numerals identify similar or identical elements. As used herein, the term "distal" refers to that portion which is further from the user while the term "proximal" refers to that portion which is closer to the user or surgeon.

The minimally invasive surgery described herein employs a device that facilitates multiple instrument access through a single incision while still allowing for triangulation. This device permits a user to operate through a single entry point, typically the patient's navel or an incision in the patient's abdomen. Additionally, the presently disclosed device may be used in a procedure where a naturally occurring orifice (e.g. vagina or anus) is the point of entry to the surgical site. The disclosed procedure involves insufflating the body cavity and positioning a portal member within, e.g., the navel of the patient. Instruments including an endoscope and additional instruments such as graspers, staplers, forceps or the like may be introduced within a portal member to carry out the surgical procedure. An example of such a surgical portal is disclosed in commonly assigned U.S. patent application Ser. No. 12/244,024, published as U.S. Publication No. 2009/0093752 A1, filed Oct. 2, 2008, the entire contents of which are hereby incorporated by reference herein.

Figure 1:
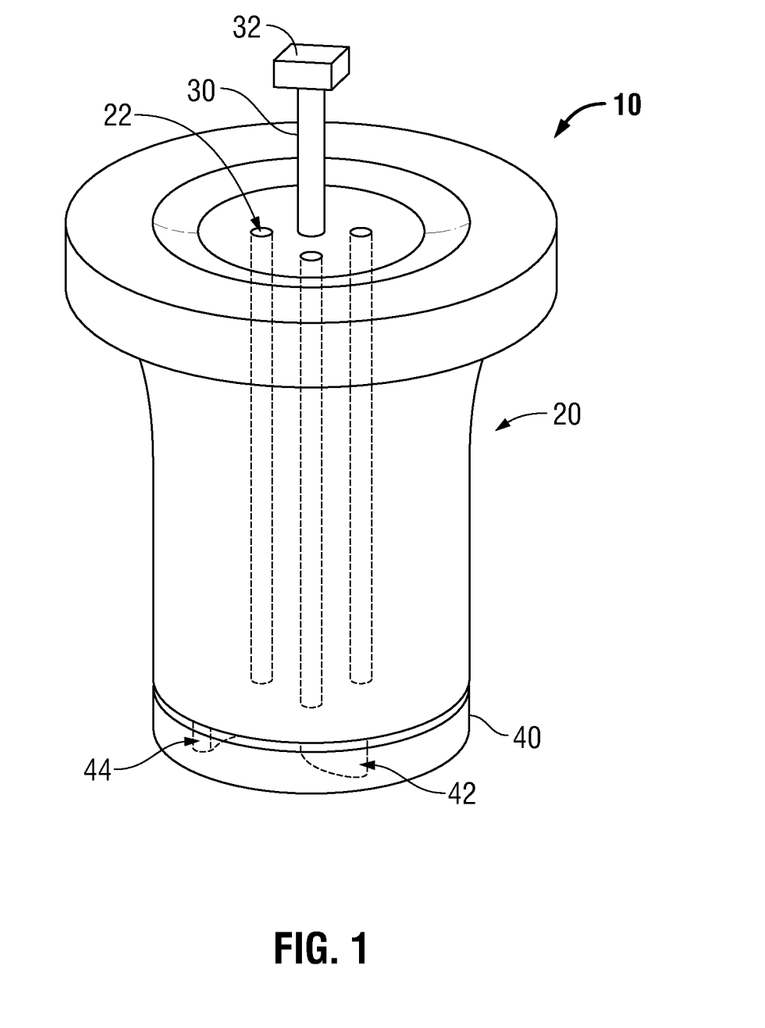
FIG. 1 is a perspective view of a surgical apparatus in accordance with the present disclosure.

Referring now to FIG. 1, a surgical apparatus 10 is disclosed including a housing 20, a rod 30 extending through housing 20, and a plate 40 attached to a distal end of rod 30. Housing 20 is adapted for sealed insertion into an incision in tissue and defines a plurality of lumens 22 therethrough for providing access to a surgical space. Lumens 22 are adapted for the sealed reception of surgical objects "S" therethrough and insufflation fluids such as, for example, $CO_2$, may be provided to maintain the surgical space. The lumens may also include a valve or valves (not shown) for maintaining a fluid-tight seal with respect to the surgical space when surgical objects "S" are removed. The valves may be, for example, flapper valves, duck-bill valves, or other valves as known in the art.

Referring now to FIGS. 1, 2, 5, 6, 7a and 7b, rod 30 extends through housing 20 along a longitudinal axis A-A (FIG. 5) and may include a handle 32 disposed at a proximal end. Handle 32 may be used by a physician to rotate rod 30 about longitudinal axis A-A or to actuate rod 30 relative to housing 20 along longitudinal axis A-A. Rod 30 may alternatively be rotated or actuated directly by the physician or may be rotated or actuated by other methods as known in the art. Housing 20 may receive rod 30 in a substantially fluid-tight manner to aid in the maintenance of a fluid-tight surgical space.

Figure 2:
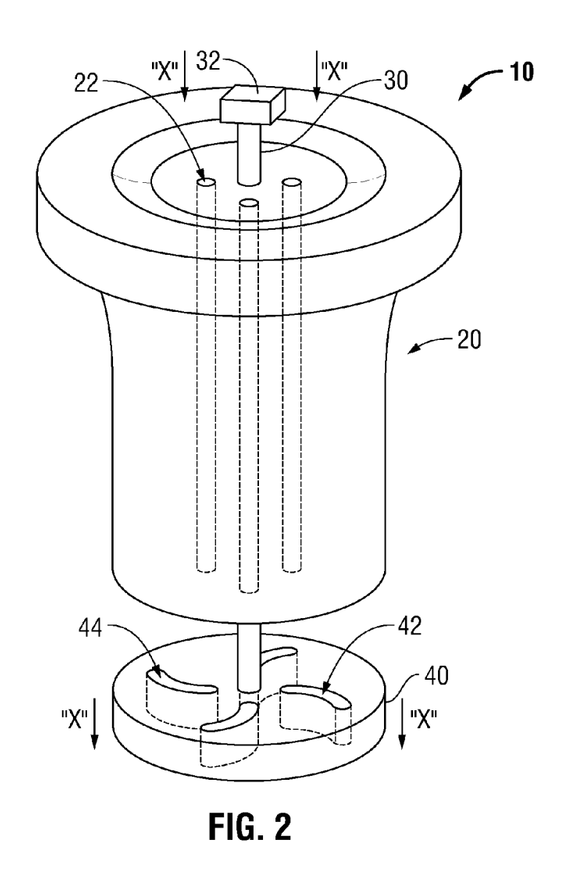
FIG. 2 is a perspective view of the surgical apparatus of FIG. 1 with the plate deployed.
Figure 3:
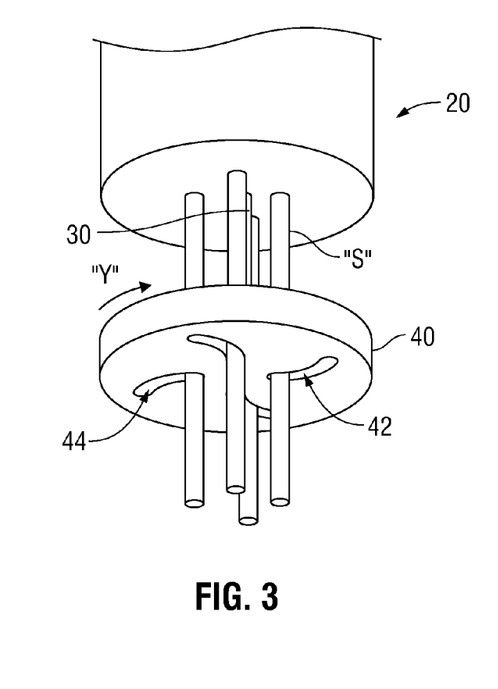
FIG. 3 is a perspective view of the distal end of the surgical apparatus of FIG. 2 showing surgical objects inserted therethrough.
Figure 5:
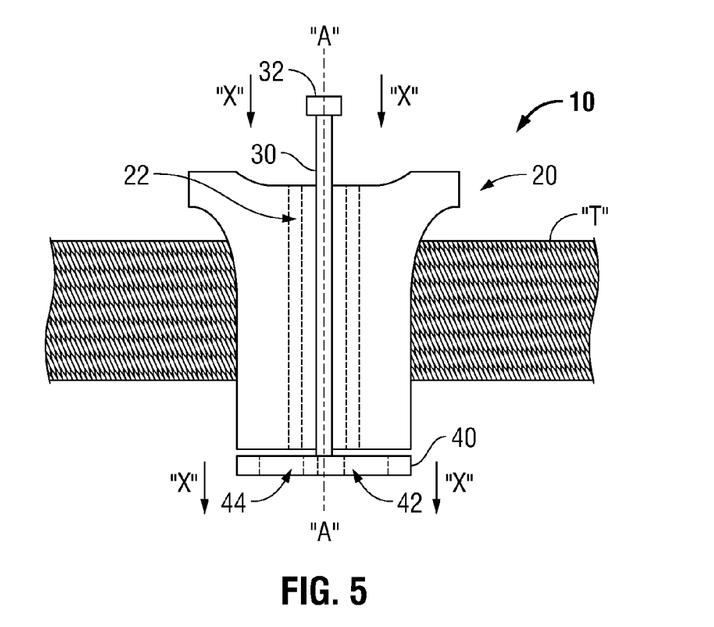
FIG. 5 is a cross-section of the surgical apparatus of FIG. 1 after insertion into an incision in tissue.
Figure 6:
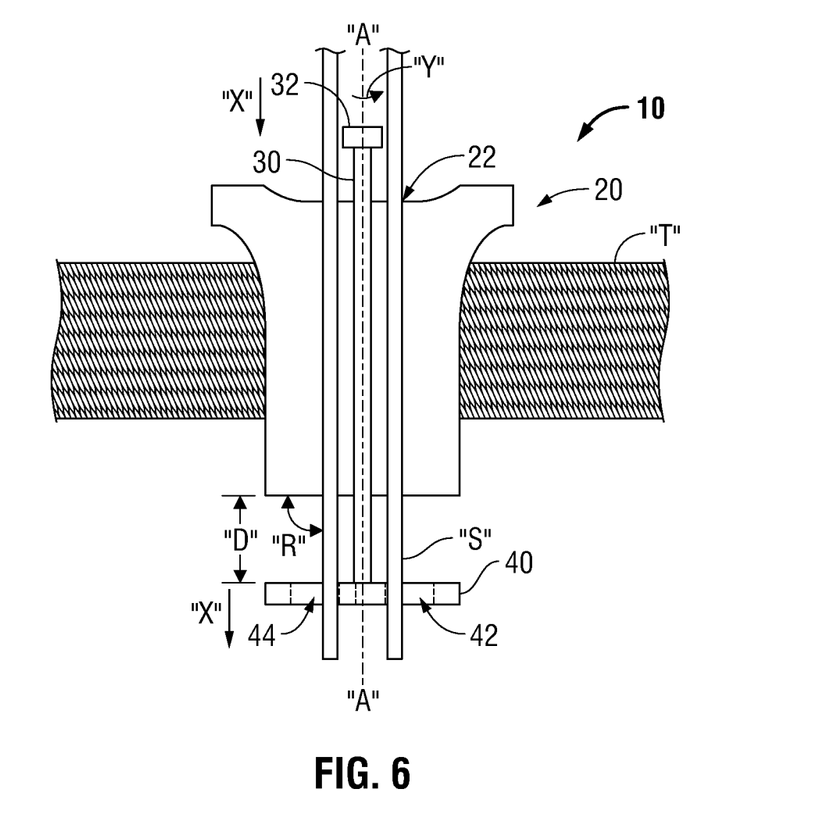
FIG. 6 is a cross-section of the surgical apparatus of FIG. 5 showing surgical objects inserted therethrough.

Referring now to FIGS. 2, 5 and 6, plate 40 is initially disposed proximate to a distal end of housing 20 (FIG. 5) and is movable relative to housing 20 along longitudinal axis A-A upon actuation of rod 30 in an axial direction "X" (FIGS. 2 and 6). Rod 30 may also include indicia (not shown) thereon to assist the physician in determining a distance "D" between plate 40 and the distal end of housing 20. The physician may actuate rod 30 to move plate 40 to different offset distances "D" (FIGS. 7a and 7b) depending on the desired triangulation positions of surgical instruments "S" as will be described in more detail below.

Referring now to FIGS. 3, 4, 7a, 7b, 8a, 8b, 8c and 9, plate 40 is rotatable about longitudinal axis A-A upon rotation of rod 30 in direction "Y" (FIGS. 3, 4, 7a and 7b) and includes a plurality of slots 42 extending therethrough. Slots 42 are dimensioned for the reception of surgical objects "S" therethrough. Each slot 42 defines a camming section or pathway 44 for guiding surgical objects "S" between a first position and a second position upon rotation of plate 40 as will be further described below. Pathways 44 may be arcuate, linear, kidney shaped, or any other geometric shape that would facilitate the transition of surgical objects "S" between the first and second positions (FIGS. 8a, 8b, 8c and 9). Pathways 44 may be configured in the same shape (FIGS. 8a, 8b and 8c) or one or more of pathways 44 may be configured in different shapes (FIG. 9) depending on the needs of the surgeon and the procedure being performed.

Figure 8A:
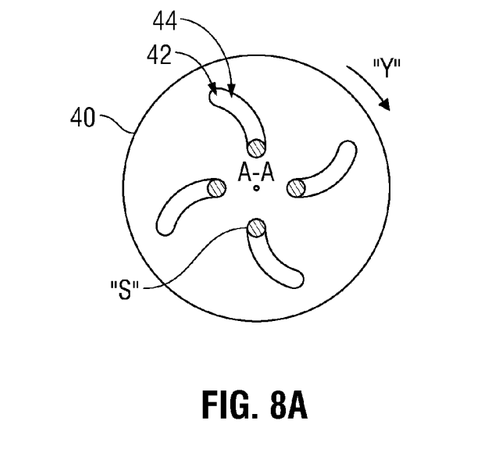
FIG. 8a is a bottom up view of the plate of the surgical apparatus of FIG. 1 with the surgical objects in the first position.
Figure 8B:
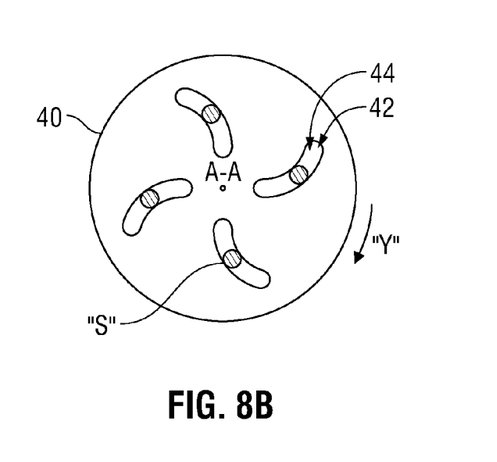
FIG. 8b is a bottom up view of the plate of the surgical apparatus of FIG. 1 with the surgical objects between the first and second positions.
Figure 8C:
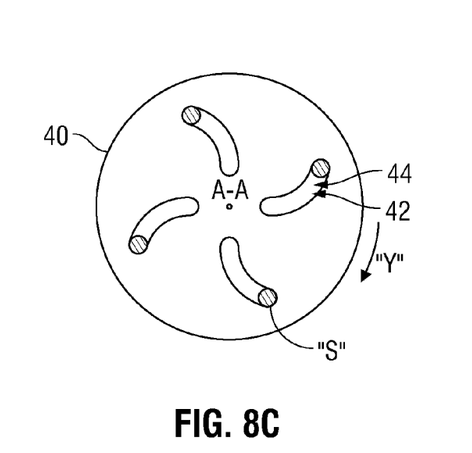
FIG. 8c is a bottom up view of the plate of the surgical apparatus of FIG. 1 with the surgical objects in the second position.
Figure 9:
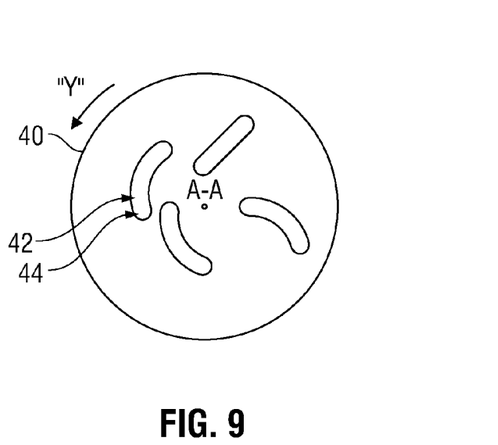
FIG. 9 is a top down view of the plate of the surgical apparatus of FIG. 1 showing an alternate slot configuration.

Each pathway 44 is adapted to guide the distal portion of a surgical object "S" between the first position where the surgical object "S" is a first radial distance from rod 30 and longitudinal axis A-A (FIG. 8a) and a second position where the surgical object "S" is a second radial distance from rod 30 and longitudinal axis A-A (FIG. 8c) upon rotation of plate 40. The first radial distance may be greater than, equal to or less than the second radial distance as shown in FIGS. 8a, 8c and 9. It is also contemplated that plate 40 may be partially rotated such that surgical objects "S" are positioned between the first and second positions at a radial distance from rod 30 and longitudinal axis A-A that is between the first and second radial distances as seen in FIG. 8b.

For example, if the location of desired surgery is off axis in one direction, one pathway 44 may be configured such that the second radial distance is longer than the first radial distance while a second pathway 44 on or near the opposite side of rod 30 and longitudinal axis A-A may be configured such that the second radial distance is shorter than the first radial distance (FIG. 9). As another example, if surgical object "S" is rigid or inflexible, pathway 44 may maintain the surgical object "S" at the same distance from rod 30 and longitudinal axis A-A when transitioning between the first and second positions to avoid bending or breaking surgical object "S" (FIG. 9).

Figure 7A:
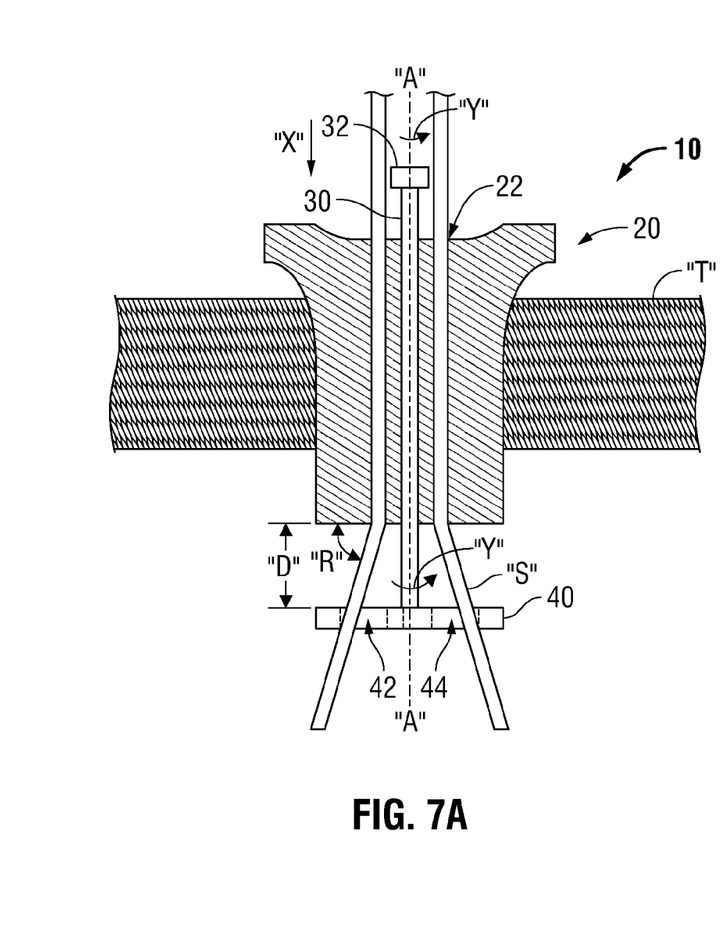
FIG. 7a is a cross-section of the surgical apparatus of FIG. 6 showing the surgical objects after the plate has been rotated with a longer distance between the plate and the housing.
Figure 7B:
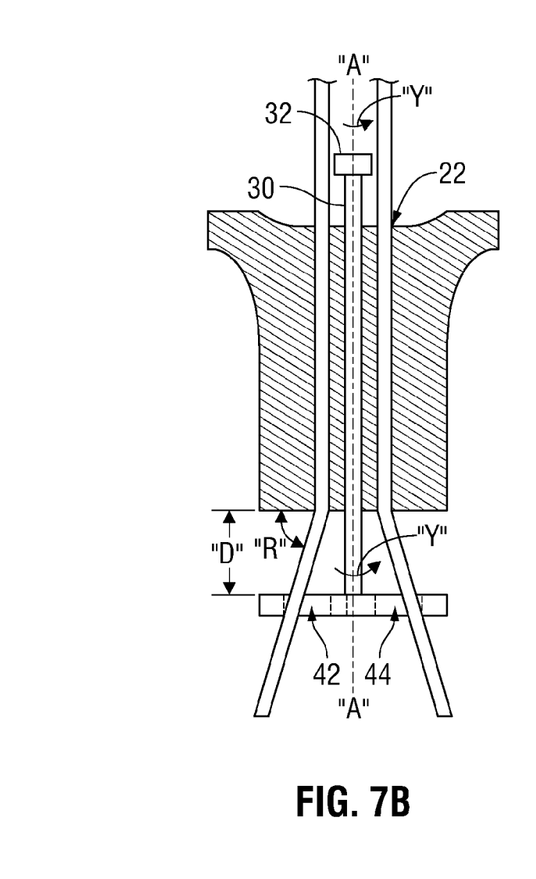
FIG. 7b is a cross-section of the surgical apparatus of FIG. 6 showing the surgical objects after the plate has been rotated with a shorter distance between the plate and the housing.

Referring now to FIGS. 6, 7a and 7b, when surgical objects "S" are in the first position they define an angle "R" relative to the distal end of housing 20 of about 90 degrees, as seen in FIG. 6. When surgical objects "S" are in the second position however the degree of angle "R" depends, in part, on the distance "D" that plate 40 is offset relative to the distal end of housing 20. When distance "D" is small, angle "R" is small and the distal ends of surgical objects "S" are thus spread farther apart, as seen in FIG. 7b. On the other hand, as distance "D" is increased, angle "R" is also increased and the distal ends of surgical objects "S" are less spread apart than when angle "R" is small, as seen in FIG. 7a. It is also contemplated that, when in the first position, angle "R" may be smaller or larger than 90 degrees. Angle "R" is also dependant on the shape of pathways 44 where, for example, a second position having a larger radial distance from rod 30 and longitudinal axis A-A will define a smaller angle "R" than a second position having a smaller radial distance.

By utilizing both rotational and axial movement of rod 30, as described above, a surgeon is able to position surgical objects "S" within the surgical space in a variety of configurations such that the triangulation of surgical objects "S" may be achieved in a reliable fashion. In particular, rotational and axial movement of rod 30 positions the distal ends of the surgical instruments in known and predictable locations relative to the housing 20 and to each other.

Although four slots 42 are shown in the various figures it is understood that plate 40 may include more slots 42 or less slots 42 and that the number of slots 42 may match the number of lumens 22 or may be different than the number of lumens 22. A portion of each slot 42 may be aligned with a respective lumen 22 when in the first position.

Plate 40 may alternatively be removably attachable to rod 30 and a selection of different plate configurations may be provided depending on the needs of the surgeon or the procedure to be performed. Plate 40 may be formed of any shape including but not limited to circular, ovoid, rectangular or any other shape capable of having slots 42 and receiving surgical objects "S" therethrough.

Figure 4:
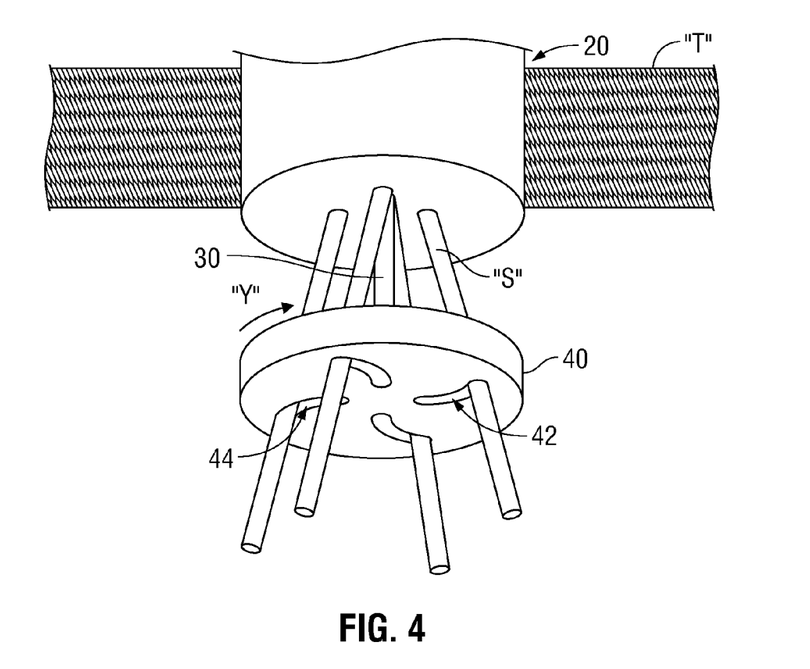
FIG. 4 is a perspective view of the distal end of the surgical apparatus of FIG. 3 showing the surgical objects after the plate has been rotated.

During use, referring now to FIGS. 3, 4, 5, 7a, 7b, 8a, 8b, 8c and 9, housing 20 is inserted into an incision in tissue "T" with plate 40 disposed at an initial position proximate to a distal end of housing 20 (FIG. 5). Alternatively plate 40 may be spaced distally from housing 20 along longitudinal axis A-A during insertion. After inserting housing 20 into the incision, one or more surgical instruments "S" are inserted through plurality of lumens 22 and plurality of slots 42. Rod 30 is then actuated in axial direction "X" to move plate 40 distally a desired distance D relative to housing 20 along longitudinal axis A-A (FIG. 6). Once plate 40 has been moved the desired amount, rod 30 is rotated in a direction "Y" to rotate plate 40 and transition surgical objects "S" along pathways 44 from the first position to the second position (FIGS. 4, 7a and 7b). Surgical objects "S" are transitioned between the first and second positions due to the shape of pathways 44 of slots 42, shown in FIGS. 8a, 8b, 8c and 9, where the rotational force applied to rod 30 and plate 40 forces surgical objects "S" along pathways 44 (FIGS. 4, 7a and 7b). In this way triangulation of the various surgical objects "S" may be achieved. Once the surgical operation is completed, rod 30 is rotated opposite to direction "Y" and surgical objects "S" are transitioned from the second position to the first position along pathways 44. Rod 30 is then actuated opposite to axial direction "X" to move plate 40 proximally relative to housing 20 along longitudinal axis A-A. Surgical objects "S" may then be removed. Once surgical objects "S" are removed, housing 20 along with plate 40 and rod 30 may be removed from the incision.

Although the subject apparatus has been described with respect to preferred embodiments, it will be readily apparent, to those having ordinary skill in the art to which it appertains, that changes and modifications may be made thereto without departing from the spirit or scope of the subject apparatus.

The invention claimed is:

1. A surgical apparatus comprising:
   a housing defining a longitudinal axis and having a plurality of lumens extending therethrough, the housing adapted for sealed insertion into an incision in tissue, the plurality of lumens adapted for sealed reception of surgical objects therethrough;
   a rod extending through the housing; and
   a plate attached to a distal end of the rod and rotatable about the longitudinal axis upon rotation of the rod, the plate including a plurality of slots dimensioned for the reception of surgical objects therethrough, at least one of the slots being adapted to transition a surgical object between a first position at a first distance from the longitudinal axis and a second position at a second distance from the longitudinal axis upon rotation of the plate, the second distance being different from the first distance.

2. The surgical apparatus of claim 1, wherein the plate is movable relative to the housing along the longitudinal axis upon actuation of the rod in an axial direction.

3. The surgical apparatus of claim 1, wherein at least one of the slots is dimensioned such that the second position is farther from the longitudinal axis than the first position.

4. The surgical apparatus of claim 1, wherein at least one of the slots is dimensioned such that the second position is closer to the longitudinal axis than the first position.

5. The surgical apparatus of claim 1, wherein at least one of the slots is dimensioned such that the second position is the same distance from the longitudinal axis as the first position.

6. The surgical apparatus of claim 1, wherein at least one of the slots defines a geometric shape.

7. The surgical apparatus of claim 1, wherein at least one of the slots defines a kidney shape.

8. The surgical apparatus of claim 1, wherein at least one of the slots defines an arcuate shape.

9. The surgical apparatus of claim 1, wherein at least one of the slots defines a linear shape.

10. The surgical apparatus of claim 1, wherein the plate is removably attachable to a distal end of the housing.

11. The surgical apparatus of claim 1, wherein a portion of each slot is aligned with a respective lumen of the plurality of lumens when in the first position.

12. The surgical apparatus of claim 1, wherein at least one slot is shaped differently than at least one other slot.

13. A method of triangulation comprising the steps of:
    providing a housing defining a longitudinal axis and having a plurality of lumens extending therethrough, the housing adapted for sealed insertion into an incision in tissue, the plurality of lumens adapted for sealed reception of surgical objects therethrough;

providing a rod extending through the housing;

providing a plate attached to a distal end of the rod and rotatable about the longitudinal axis upon rotation of the rod, the plate adapted for movement relative to the housing along the longitudinal axis upon actuation of the rod in an axial direction and including a plurality of slots dimensioned for the reception of surgical objects therethrough, at least one of the slots being adapted to transition a surgical object between a first position at a first distance from the longitudinal axis and a second position at a second distance from the longitudinal axis upon rotation of the plate, the second distance being different from the first distance;

inserting surgical objects through one or more of the lumens and slots; and rotating the rod, whereby the plate is rotated and the surgical objects are transitioned between the first position and the second position.

14. The method of claim 13, wherein at least one of the slots is dimensioned such that the second position is farther from the longitudinal axis than the first position.

15. The method of claim 13, wherein at least one of the slots is dimensioned such that the second position is closer to the longitudinal axis than the first position.

16. The method of claim 13, wherein at least one of the slots is dimensioned such that the second position is the same distance from the longitudinal axis as the first position.

17. The surgical apparatus of claim 13, wherein at least one slot defines a geometric shape.

18. The surgical apparatus of claim 13, wherein at least one slot defines a kidney shape.

19. The method of claim 13, wherein at least one of the slots is arcuate.

20. The method of claim 13, wherein at least one of the slots is linear.

21. The method of claim 13, further including actuating the rod axially, whereby the plate is moved relative to the housing along the longitudinal axis.

22. A surgical apparatus comprising:

a housing defining a longitudinal axis and having a lumen extending therethrough, the housing adapted for sealed insertion into an incision in tissue, the lumen adapted for sealed reception of a surgical object therethrough;

a rod extending through the housing; and a plate attached to a distal end of the rod and rotatable about the longitudinal axis upon rotation of the rod, the plate including a slot dimensioned for the reception of a surgical object therethrough, the slot being adapted to transition a surgical object between a first position at a first distance from the longitudinal axis and a second position at a second distance from the longitudinal axis upon rotation of the plate, the second distance being different from the first distance.

\* \* \* \* \*